United States Patent [19]

Harbridge et al.

[11] Patent Number: 4,562,182
[45] Date of Patent: Dec. 31, 1985

[54] COMPOUNDS CONTAINING BETA-LACTAMS

[75] Inventors: John B. Harbridge, Coulsdon; Irene Stirling, Reigate, both of England

[73] Assignee: Beecham Group p.l.c., England

[21] Appl. No.: 328,736

[22] Filed: Dec. 8, 1981

[30] Foreign Application Priority Data

Dec. 23, 1980 [GB] United Kingdom ............... 8041274

[51] Int. Cl.⁴ .................. C07D 487/04; A61K 31/42
[52] U.S. Cl. ............................. 514/210; 260/245.3
[58] Field of Search ................ 260/239 A, 245.3; 424/272; 514/210

[56] References Cited

U.S. PATENT DOCUMENTS

| | | | |
|---|---|---|---|
| 3,926,955 | 12/1975 | Burton et al. | 424/271 |
| 4,093,626 | 6/1978 | Hunt | 260/245.3 |
| 4,229,443 | 10/1980 | Binderup | 424/200 |
| 4,231,928 | 11/1980 | Naito et al. | 424/251 |
| 4,237,051 | 12/1980 | McCombie | 260/245.2 R |
| 4,244,965 | 1/1981 | Howarth et al. | 424/272 |
| 4,246,262 | 1/1981 | Vangedal | 424/244 |
| 4,252,722 | 2/1981 | Melilo et al. | 424/274 |
| 4,278,686 | 7/1981 | Corbett et al. | 424/274 |
| 4,315,006 | 2/1982 | Storer | 424/250 |
| 4,315,935 | 2/1982 | Ali | 424/258 |
| 4,316,907 | 2/1982 | Oxford et al. | 549/60 |
| 4,317,826 | 3/1982 | Gleason | 424/258 |
| 4,317,835 | 3/1982 | Van Dijk et al. | 424/309 |
| 4,321,254 | 3/1982 | Ali | 424/40 |
| 4,341,786 | 7/1982 | Demarinis et al. | 424/258 |
| 4,350,685 | 9/1982 | Ali et al. | 424/48 |
| 4,351,842 | 9/1982 | Coles | 424/274 |
| 4,352,809 | 10/1982 | Bondinell et al. | 424/258 |
| 4,366,167 | 12/1982 | Corbett | 424/274 |
| 4,379,787 | 4/1983 | Lunn et al. | 424/246 |
| 4,382,084 | 5/1983 | Ponsford et al. | 424/114 |
| 4,382,932 | 5/1983 | Lunn et al. | 424/246 |
| 4,385,047 | 5/1983 | Ali | 424/43 |
| 4,388,316 | 6/1983 | Lunn et al. | 424/246 |
| 4,393,072 | 7/1983 | Merkel et al. | 424/275 |
| 4,395,406 | 7/1983 | Gacek et al. | 424/180 |
| 4,395,421 | 7/1983 | Taylor et al. | 424/283 |
| 4,396,619 | 8/1983 | Lunn et al. | 424/246 |
| 4,396,620 | 8/1983 | Lunn | 424/246 |
| 4,397,845 | 8/1983 | Allen | 424/180 |
| 4,399,142 | 8/1983 | Durant et al. | 424/258 |
| 4,401,665 | 8/1983 | Sheinaus et al. | 424/233 |
| 4,401,668 | 8/1983 | Lunn | 424/240 |
| 4,402,949 | 9/1983 | Hartmann et al. | 424/183 |
| 4,402,955 | 9/1983 | Lunn | 424/246 |
| 4,402,974 | 9/1983 | Matier et al. | 424/308 |
| 4,402,976 | 9/1983 | Muir | 424/311 |
| 4,405,596 | 9/1983 | Helbig et al. | 424/33 |
| 4,406,898 | 9/1983 | Lunn et al. | 424/240 |
| 4,406,899 | 9/1983 | Aburaki et al. | 424/246 |
| 4,411,907 | 10/1983 | Toia | 424/273 B |
| 4,411,909 | 10/1983 | Gonella | 424/275 |
| 4,414,204 | 11/1983 | Tarcsay et al. | 424/127 |
| 4,421,760 | 12/1983 | Box | 424/274 |
| 4,427,690 | 1/1984 | Cole et al. | 424/272 |
| 4,428,958 | 1/1984 | Ponsford | 424/272 |
| 4,444,754 | 4/1984 | Stirling et al. | 424/114 |
| 4,444,783 | 4/1984 | Eglington | 424/114 |
| 4,446,146 | 5/1984 | Southgate et al. | 424/274 |

OTHER PUBLICATIONS

Bentley et al., Chem. Abs. 92, 58657k, (1979).

Primary Examiner—Mark L. Berch
Attorney, Agent, or Firm—Jacobs & Jacobs

[57] ABSTRACT

A compound of formula (I) or a salt or ester thereof:

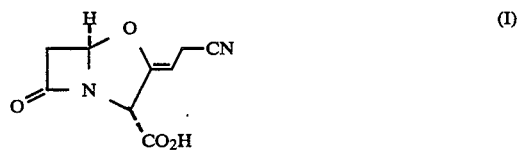

Pharmaceutical compositions comprising a compound of formula (I) or a pharmaceutically acceptable salt or pharmaceutically acceptable ester thereof are also disclosed.

14 Claims, No Drawings

COMPOUNDS CONTAINING BETA-LACTAMS

This invention relates to a class of novel β-lactam compounds, to the process for their preparation and to pharmaceutical compositions containing them.

U.K. Pat. Nos. 1,508,977 and 1,508,978 disclose inter alia clavulanic acid and its salts and esters. Clavulanic acid has the formula (A):

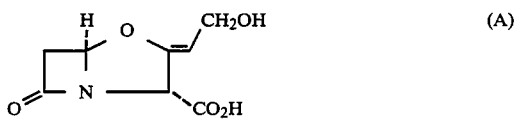

We have now found a novel class of compounds containing the cyanide group, which have anti-bacterial and β-lactamase inhibitory activity.

Accordingly, the present invention provides a compound of formula (I) or a salt or ester thereof:

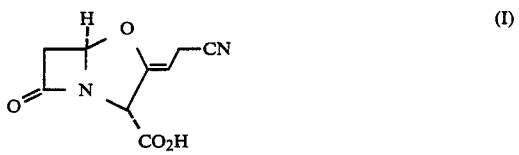

The major utility of the compound of formula (I) is as a pharmaceutical and, accordingly, the salts and esters of the compound of formula (I) are preferably pharmaceutically acceptable. The compound of formula (I) may also be used as an anti-bacterial of β-lactamase inhibitor in non-pharmaceutical uses such as, for example, as a disinfectant or paint additive; those salts and esters which are not normally considered to be pharmaceutically acceptable are suitable for this application.

Suitable pharmaceutically acceptable salts of the compound of formula (I) include metal salts, e.g. aluminium, alkali metal salts such as sodium or potassium, alkaline earth metal salts such as calcium or magnesium and ammonium or substituted ammonium salts, for example those with lower alkylamines such as triethylamine, cycloalkylamines such as bicyclohexylamine, or with dibenzylamine, N,N-dibenzylethylenediamine, 1-ephenamine, N-ethylpiperidine, or N-benzyl-β-phenethylamine.

Particularly suitable pharmaceutically acceptable salts of the compound of formula (I) are the alkali metal salts such as lithium, sodium and potassium. The preferred pharmaceutically acceptable salts are the sodium and potassium salts.

Examples of suitable pharmaceutically acceptable groups include those which break down readily in the human body to leave the parent acid or its salt, for example acyloxyalkyl groups such as acetoxymethyl, pivaloyloxymethyl, α-acetoxyethyl and α-pivaloyloxyethyl groups; alkoxycarbonyloxyalkyl groups, such as ethoxycarbonyloxymethyl; dialkylamino alkyl groups such as dimethylaminomethyl, dimethylaminoethyl, diethylaminomethyl or diethylaminoethyl; and α-ethoxycarbonyloxyethyl; and lactone groups such as phthalidyl or dimethoxyphthalidyl.

The present invention also provides a pharmaceutical composition which comprises a compound of this invention and a pharmaceutically acceptable carrier.

The compositions of the invention include those in a form adapted for oral, topical or parenteral use and may be used for the treatment of the infection in animals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating anti-biotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form.

The injectable solution of the compound of this invention may be made up in a sterile pyrogen-free liquid such as water, aqueous ethanol or the like.

An alternative approach to administering the compounds of this invention is to utilise an injectable suspension. Such suspensions may be made up in sterile water; sterile saline or the like, and may also contain suspending agents such as polyvinylpyrrolidone, lecithin or the like. Alternatively such compositions may be prepared in an acceptable oil suspending agent such as arachis oil or its equivalent. For use in such suspensions the compounds of this invention should be in the form of find particles.

Unit dose compositions comprising a compound of this invention adapted for oral administration form a further suitable composition aspect of this invention.

Unit dose compositions comprising a compound of this invention adapted for topical administration are also presented by this invention. In this instance 'topical administration' also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or cephalosporin. Considerable advantages accrue from the inclusion of a penicillin or cephalosporin which shows instability to β-lactamases since the resulting composition shows enhanced effectiveness (synergy). Suitable penicillins, cephalosporins or other β-lactam anti-biotics for inclusion in such synergistic compositions include not only those known to be highly susceptible to β-lactamases but also those which have a degree of intrinsic resistance to β-lactamases.

Suitable penicillins for inclusion in the compositions of this invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, pipericillin, and other known penicillins including pro-drugs therefor such as their in vivo hydrolysable esters such as the acetoxymethyl, pivaloyloxymethyl, α-ethoxycarbonyloxyethyl or phthalidyl esters of ampicillin, benzylpenicillin or amoxycillin, and aldehyde of ketone adducts of penicillins containing a 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include cefatrizine, cephaloridine, cephalothin, cefazolin, cephalexin, cephacetrile, cephamandole nafate, cephapirin, cephradine, 4-hydroxycephalexin, cefaparole, cephaloglycin, cefoperazone and other known cephalosporins or pro-drugs thereof.

Such compounds are frequently used in the form of a salt or hydrate of the like.

Naturally if the penicillin or caphalosporin present in the composition is not suitable for oral administration then the composition will be adapted for parenteral administration.

Highly favoured penicillins for use in the compositions of this invention include ampicillin, amoxycillin, carbenicillin and ticarcillin. Such penicillins may be used as a pharmaceutically acceptable salt such as the sodium salt. Alternatively the ampicillin or amoxycillin may be used in the form of find particles of the zwitterionic form (generally as ampicillin trihydrate or amoxycillin trihydrate) for use in an injectable suspension, for example in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin which may be in the form of a pharmaceutically acceptable salt for example the sodium salt.

When present together with a cephalosporin or penicillin, the ratio of a compound of the invention to the penicillin or cephalosporin agent may vary over a wide range of ratios, such as from 10:1 to 1:10 for example about 3:1, 2:1, 1:1, 1:2, 1:3, 1:4, 1:5 or 1:6, (wt/wt, based on pure free anti-biotic equivalent). Orally administrable compositions containing a compound of the invention will normally contain relatively more synergist than corresponding injectable compositions.

The total quantity of a compound of the invention in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia the respiratory tract, the urinary tract and soft tissues in humans and mastitis in cattle.

Normally between 50 and 3000 mg of the compounds of the invention will be administered each day of treatment but more usually between 100 and 1000 mg of the compounds of the invention will be administered per day, for example at 1–6 doses, more usually as 2, 3 or 4 doses. However, for the treatment of more severe systemic infections or infections of particularly intransigent organisms higher doses may be used in accordance with clinical practice.

The penicillin or cephalosporin in the synergistic composition of this invention will normally be present at approximately the amount at which it is conventionally used which will usually be expected to be from about 62.5 to 3000 mg per dose, more usually about 125, 250, 500 or 1000 mg per dose.

One particularly favoured composition of this invention will contain from 150 to 1000 mg of amoxycillin as the trihydrate or sodium salt and from 25 to 500 mg of a compound of this invention.

A further particularly favoured composition of this invention will contain from 150 to 1000 mg of ampicillin or a pro-drug therefor and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride, or talampicillin hydrochloride. Most suitably this form of the composition will contain a compound of the formula (I) when in crystalline form.

Most suitably the preceding composition will contain from 200 to 700 mg of the penicillin component. Most suitably the preceding composition will comprise from 50 to 250 mg of a compound of the formula (I) preferably in crystalline form.

Such compositions may be adapted for oral or parenteral use except when containing an in vivo hydrolysable ester of ampicillin or amoxycillin in which case the compositions will not be adapted for parenteral administration.

Another particularly favoured composition of this invention will contain from 200 to 2000 mg of carbenicillin, ticarcillin or a pro-drug therefor and from 50 to 500 mg of a compound of the invention.

Suitably this form of composition will contain di-sodium carbenicillin. Suitably this form of the composition will contain di-sodium ticarcillin.

More suitably this form of the composition will contain from 75 to 250 mg of a compound of the formula (I) preferably in crystalline form. Such compositions containing di-salts of carbenicillin and ticarcillin will be adapted for parenteral administration.

The present invention also provides a method of treating bacterial infections in humans or animals including domestic mammals which comprises the administration of a composition of this invention.

Commonly the infection treated will be due to a strain of *Staphylococcus aureus, Klebsiella aerogenes, Escherichia coli, Proteus sp., Bacteroides fragilis* or the like. The organisms believed to be most readily treated by an antibacterially effective amount of a compound of this invention is *Staphylococcus aureus*. The other organisms named are more readily treated by using a synergistically effective amount of the compound of the invention and a penicillin or cephalosporin. The administration of the two components may take place separately but in general we prefer to use a composition containing both the synergist and the penicillin or cephalosporin.

The indications for treatment include respiratory tract and urinary tract infections in humans and mastitis in cattle.

The present invention also provides a process for the preparation of a compound of formula (I) or a salt or ester thereof, which process comprises reacting a compound of formula (II):

$$\text{(II)}$$

wherein $R^x$ is a carboxy protecting group, with
 (i) hydrogen cyanide;
 (ii) a compound of formula (III):

$$R^1OCON=NCOOR^2 \quad (III)$$

wherein $R^1$ and $R^2$ are independently $C_{1-6}$ alkyl, aryl or aryl($C_{1-6}$)alkyl; and (iii) a compound of formula (IV):

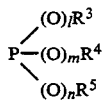

$$(IV)$$

wherein l, m and n are independently 0 or 1 and $R^3$, $R^4$ and $R^5$ are each independently $C_{1-6}$ alkyl, aryl($C_{1-6}$alkyl or aryl; and thereafter where necessary carrying out one or more of the following steps:

(a) removing the carboxy protecting group $R^x$
(b) converting a salt to the free carboxylic acid or to an ester, or to a different salt.

Suitable compounds of the formula (III) include those wherein $R^1$ and $R^2$ are independently selected from methyl, ethyl, propyl, butyl, phenyl and benzyl groups. It is generally convenient that $R^1$ and $R^2$ represent the same moiety. Particularly suitable compounds of the formula (III) include those wherein $R^1$ and $R^2$ each represent an ethyl, t-butyl or isopropyl group.

Suitable compounds of the formula (IV) include those wherein the $R^3$, $R^4$ and $R^5$ groups are selected from methyl, ethyl, n-propyl, n-butyl, benzyl, phenyl and methoxyphenyl groups. It is generally convenient that $R^3$, $R^4$ and $R^5$ each represent the same moiety. Favoured compounds of formula (IV) include tri-arylphosphines and tri-alkylphosphites. Particularly suitable compounds of the formula (IV) include triphenylphosphine, trimethylphosphite, tri-ethylphosphite and tri-p-methoxyphenylphosphine.

Suitable carboxy protecting groups for the group —$CO_2R^x$ in formula (II) include ester derivatives of the carboxylic acid. The derivative is preferably one which may readily be cleaved at a later stage of the reaction.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-benzyl, 4-pyridylmethyl, allyl, diphenylmethyl, triphenymethyl, 2-benzyloxyphenyl, 4-methylthiophenyl, methoxymethyl, a silyl, or phosphorus-V-containing group, or methyl or ethyl.

The carboxylic group or a salt thereof may be regenerated from any of the above esters by usual methods appropriate to the particular $R^x$ group, for example, base-catalysed hydrolysis, or by enzymically-catalysed hydrolysis, or by hydrogenation.

The preceding reaction normally takes place in a solvent inert under the reaction conditions such as toluene, dichloromethane, tetrahydrofuran or dioxane. The reaction is generally carried out at a depressed or non-elevated temperature, for example −80° C. to +30° C., and preferably at a depressed temperature, for example −20° to 0° C., and conveniently at about 0° C.

Acids within formula (I) may also be prepared by the careful acidification of a corresponding salt such as the sodium salt.

Salts within formula (I) may be prepared by treatment of an acid within formula (I) with, for example, sodium ethyl hexanoate or potassium ethyl hexanoate. Salts within formula (I) may also be prepared by salt exchange in conventional manner, for example a solution of the lithium salt in water may be passed through a bed of ion exchange resin in the sodium form (e.g. Amberlite 120; a sodium salt of a sulphonated polystyrene divinyl benzene co-polymer) in about ten-fold excess until elution is complete; the resulting sodium salt may be obtained by freeze drying or by evaporation to crystallisation. Similarly, a sodium salt may be converted to a lithium salt or to a potassium salt in similar manner.

The following Examples illustrate the invention.

EXAMPLE 1

Benzyl 9-cyanodeoxyclavulanate

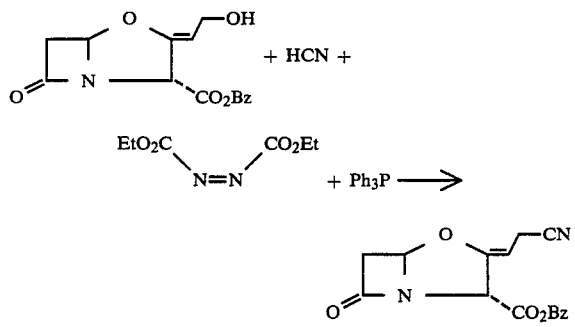

A solution of benzyl clavulanate (2.89 g; 0.01 ml) in dry tetrahydrofuran (50 ml) was treated with triphenylphosphine (3.14 g; 0.012 mol) and the mixture cooled to 0° C. A solution of hydrogen cyanide in tetrahydrofuran (12 ml of 0.97 M solution) was added, followed by the dropwise addition of diethyl azodicarboxylate. The reaction mixture was stirred at 0° for two hours; then concentrated to small volume in vacuo. The crude material was fractionated on silica gel and the product eluted with ethyl acetate:cyclohexane, 1:2. Fractions containing the product Rf(SiO$_2$/ethyl acetate:cyclohexane, 1:2=0.44 were combined and evaporated to give the title compound as a colourless oil in 5% yield.

$\nu_{max}$ (film) 2250, 1800, 1745, 1700 cm$^{-1}$; $\beta$(CDCL$_3$) 3.04 (1H, d, J 17 Hz, 6$\beta$-CH), 3.1 (2H, d, J 7 Hz, 9-CH$_2$), 3.5 (1H, dd, J 17 and 3 Hz, 6$\alpha$-CH), 4.62 (1H, bt, J 7 Hz, 8-CH), 5.09 (1H, bs, 3-CH), 5.19 (2H, s, CH$_2$C$_6$H$_5$), 5.72 (2H, d, J 3 Hz, 5-CH), 7.36 (5H, s, Ar-H), m+298.0942 C$_{16}$H$_{14}$N$_2$O$_4$ requires 298.0951.

EXAMPLE 2

Lithium 9-cyanodeoxyclavulanate

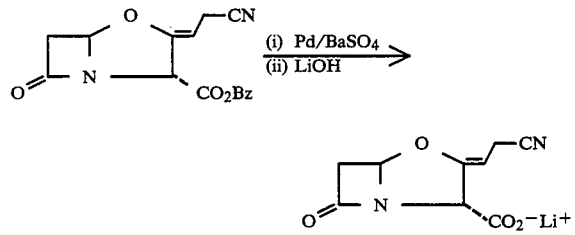

Benzyl 9-cyanodeoxyclavulanate (60 mg) in dry tetrahydrofuran (15 ml) was hydrogenolysed over 10% palladium on barium sulphate (30 mg) for one hour. The catalyst was filtered off, washed with water, and the combined filtrates brought to pH 7–8 with 1M lithium hydroxide. The aqueous solution was evaporated and the crude product chromatographed on silica gel eluting with ethyl acetate:propan-2-ol:water: 5:4:2. Fractions containing the product Rf(SiO$_2$/EtOAc:IPA:H$_2$O, 5:4:2)=0.48 were combined and evaporated to yield the required product as an off-white solid (58%).

$\nu_{max}$(KBr) 2250, 1775, 1698, 1620 cm$^{-1}$. δ(DMF -d$^7$). 3.0 (1H, d, J 17 Hz, partly obsecured by DMF peak), 3.29 (2H, m, 9-CH$_2$), 3.61 (1H, dd, J 17 and 3 Hz, 6α-CH), 4.78 (1H, dt, J 7 and 1.5 Hz, 8-CH partly obsecured by singlet at 4.79), 4.79 (1H, s, 3-CH), 5.82 (1H, d, 3 Hz, 5-CH).

EXAMPLE 3 p-Nitrobenzyl 9-cyanodeoxyclavulanate

To a solution of lithium 9-cyanodeoxyclavulanate (25 mg) in N,N-dimethylformamide (2ml) was added an excess of p-nitrobenzyl bromide. The reaction mixture was stirred at ambient temperature overnight. The solvent was removed by evaporation in vacuo, and the residue partitioned between water (20 ml) and ethyl acetate (20 ml). The solvent layer was separated, dried over anhydrous Na$_2$SO$_4$ and evaporated. The residue was subjected to chromatography on a column of silica gel, eluting with 1:1 ethyl acetate - cyclohexane. Fractions containing the desired product (by tlc, visualised by 0.02 M KMnO$_4$) were combined and evaporated to low volume, whereupon the title compound crystallised. After trituration with ether, there remained 15 mg of the compound as an almost colourless crystalline solid.

Ir (Nujol mull) 2250, 1790, 1778, 1750, 1700 cm$^{-1}$ Nmr (CDCl$_3$) 3.14 (1H, dd, J 0.7 and 17 Hz, 6-β-CH), 3.17 (1H, ddd, J 1.1, 3 and 7 Hz, 9-CH$_2$), 3.56 (1H, dd, J, 17 and 2.7 Hz, 6-α-CH), 4.65 (dt, J, 1.1 and 7 Hz, 8-CH), 5.15 (1H, m, 3-CH), 5.31 (2H, s, PhCH$_2$), 5.76 (1H, d, J 3 Hz, 5-CH), 7.57 (2H, d, J 7 Hz, C$_6$H$_2$), 8.28 (2H, m, C$_6$H$_2$).

EXAMPLE 4

Sodium 9-cyanodeoxyclavulanate

A solution of lithium 9-cyanodeoxyclavulanate (25 mg) in water (about 10 ml) was passed slowly through a thoroughly backwashed bed of 'Amberlite' IR 120 (Na+) standard grade) resin (25 ml of wet resin). A total of 50 ml of eluate was collected. This was freeze-dried overnight to afford a small quantity of pale brown glass ($\sim$20 mg). This had Ir spectrum (Nujol mull with some NaCl) which contained, among others, the following peaks. 2255, 1782, 1700 and 1620 cm$^{-1}$.

BIOLOGICAL DATA

Synergistic activity in vitro of some of the Compounds of the present invention.

| Compound | Inhibitor Conc (μg/ml) | Staph. aureus Russell | Klebsiella aerogenes E70 | E. coli JT 39 |
|---|---|---|---|---|
| Amoxycillin alone | — | 500 | 125 | 2000 |
| Amoxycillin with | 5 | 0.08 | 0.8 | 1 |
| Compound of Example No 2 | 1 | 0.30 | 1.5 | 4 |

We claim:
1. A compound of the formula (I):

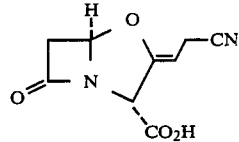

a salt thereof or a pharmaceutically acceptable ester thereof.

2. A compound according to claim 1 in the form of a pharmaceutically acceptable salt or a pharmaceutically acceptable ester.

3. A compound according to claim 1 in the form of an alkali metal salt.

4. A compound according to claim 1 in the form of the sodium or potassium salt.

5. A compound according to claim 1 in the form of the lithium salt.

6. A compound according to claim 1 which is benzyl 9-cyanodeoxyclavulanate, lithium 9-cyanodeoxyclavulanate, p-nitrobenzyl 9-cyanodeoxyclavulanate or sodium 9-cyanodeoxyclavulanate.

7. A pharmaceutical composition useful for treating bacterial infections in humans and animals and for effecting β-lactamase inhibition in humans and animals which comprises an antibacterially effective amount or a β-lactamase inhibitory amount of a compound of the formula (I):

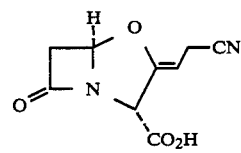

a pharmaceutically acceptable salt thereof or a pharmaceutically acceptable ester thereof, in combination with a pharmaceutically acceptable carrier.

8. A composition according to claim 7 wherein the compound is in the form of a pharmaceutically acceptable salt or pharmaceutically acceptable ester.

9. A composition according to claim 7 wherein the compound is in the form of the sodium or potassium salt.

10. A composition according to claim 7 wherein the compound is benzyl 9-cyanodeoxyclavulanate, p-nitrobenzyl 9-cyanodeoxyclavulanate or sodium 9-cyanodeoxyclavulanate.

11. A method of treating bacterial infections in humans and animals which comprises administering to a human or animal in need thereof, an antibacterially effective amount of a compound of the formula (I):

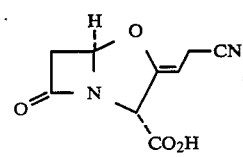

a pharmaceutically acceptable salt thereof or a pharmaceutically acceptable ester thereof, in combination with a pharmaceutically acceptable carrier.

12. A method according to claim 11 wherein the compound is in the form of a pharmaceutically acceptable salt or pharmaceutically acceptable ester.

13. A method according to claim 11 wherein the compound is in the form of the sodium or potassium salt.

14. A method according to claim 11 wherein the compound is benzyl 9-cyanodeoxyclavulanate, p-nitrobenzyl 9-cyanodeoxyclavulanate or sodium 9-cyanodeoxyclavulanate.

* * * * *